United States Patent
Ronn

[11] Patent Number: 5,843,790
[45] Date of Patent: *Dec. 1, 1998

[54] METHOD FOR ASSAYING PHOTOSENSITIZING DRUG IN WHOLE BLOOD

[76] Inventor: Avigdor M. Ronn, 27A Bond St., Great Neck, N.Y. 11021

[*] Notice: The term of this patent shall not extend beyond the expiration date of Pat. No. 5,846,834.

[21] Appl. No.: 777,573

[22] Filed: Dec. 31, 1996

[51] Int. Cl.⁶ .................................................. G01N 21/00
[52] U.S. Cl. ......................... 436/164; 356/39; 356/317; 356/318; 600/310; 600/322; 600/476; 600/477
[58] Field of Search .................................. 436/164, 172, 436/179; 422/82.05, 82.08, 82.09; 128/633, 637, 665; 356/39, 300, 311, 317, 318; 600/310, 322, 476, 477; 250/458.1, 459.1

[56] References Cited

U.S. PATENT DOCUMENTS

| | | | |
|---|---|---|---|
| 3,916,205 | 10/1975 | Kleinerman | 250/461.2 |
| 5,015,463 | 5/1991 | Dougherty et al. | 424/9.61 |
| 5,205,291 | 4/1993 | Potter | 600/431 |
| 5,589,932 | 12/1996 | Garcia-Rubio et al. | 356/39 |

OTHER PUBLICATIONS

Ronn et al. "Interspecies Pharmacokinetics . . . " Proceedings of SPIE, vol. 2625, pp. 118–123, 1996.
Ronn et al. "Meso–tetra(hydroxypheny) chlorin . . . " Proceedings of SPIE, vol. 2133, pp. 112–115,1994.
Lofgren et al. "Efficacy of Intravenous . . . " British Journal of Cancer, vol. 72, pp. 857–864, 1995.

*Primary Examiner*—Maureen M. Wallenhorst
*Attorney, Agent, or Firm*—Christopher R. Pastel; Shu Muk Lee

[57] ABSTRACT

A concentration of a photosensitizing drug in a patient, for PhotoDynamic Therapy treatment of the patient by a treatment light at a treatment light wavelenght, is determined by the steps of drawing a blood sample from the patient, spreading the blood sample between two optically transmissive plates to form a spread sample, irradiating the spread sample with an interrogation light at an interrogation wavelength range of an absorption band bluer than the treatment light wavelength, measuring a magnitude of an emission signal at the treatment light wavelength, the emission signal caused by the irradiation of the spread sample, and comparing the measured magnitude to a magnitude/concentration calibration curve to determine the concentration of the photosensitizing drug.

18 Claims, 1 Drawing Sheet

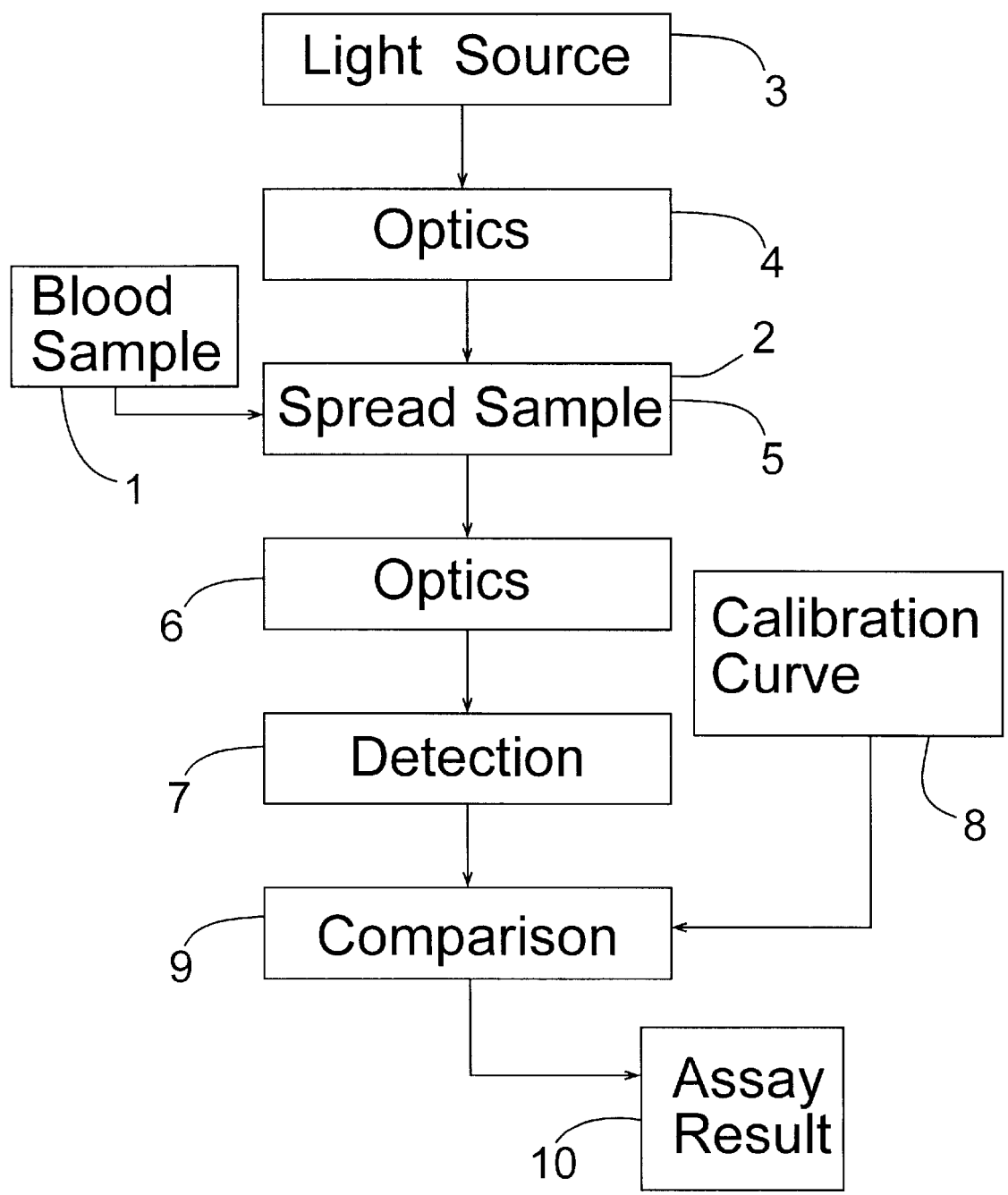

METHOD FOR ASSAYING PHOTOSENSITIZING DRUG IN WHOLE BLOOD

BACKGROUND

This invention is directed to a method for assaying a drug in whole blood. In particular, this invention is directed to a method for assaying a photosensitizing drug in whole blood rapidly through the use of fluorescence.

One known treatment for illnesses such as carcinomas and tumors is PhotoDynamic Therapy (PDT). PDT is presently used as primary or adjunctive treatment for benign or malignant tumors. PDT is based on activation, by light, of the photosensitive drug that is in the patient. The treatment involves the introduction of a photosensitive drug into a patient. Typically, the drug is disproportionately concentrated in the target abnormal cells. Such concentrating of the photosensitive drug causes a photosensitization of the patient. In particular, the target abnormal cells are photosensitized more than normal cells.

Accordingly, a source of light is shone at the patient, usually locally directed at the tumor composed of target abnormal cells. The light is tailored to the drug in order to cause a response of the drug to the light. The response of the drug, generally a chemical activation, causes a cascade of events that eventually results in the destruction of the tumor, often by the disruption of the target abnormal cell.

PDT can be given on an ambulatory basis and is often non-invasive. As such, the therapy can significantly reduce the high cost of more traditional treatments and eliminate the long term and often disabling side effects associated with such traditional treatments as radical surgery, radiotherapy, and chemotherapy.

PDT requires the concerted action of a sensitizing drug and an activating light. Neither component alone, as used in PDT, can cure the tumor or harm the healthy tissue. However, with the two components together, the technique powerfully destroys tumor cells selectively. There has been extensive development of technological improvements in both light sources and novel photochemical sensitizers such that commercially available high power compact lasers are used with drugs with improved tumor tissue to healthy tissue selectivity. Further, drugs having shorter half lives are continuing to be developed in order to minimize the time a patient is hyper photosensitive. Such photosensitivity often prevents a patient from outdoor activity because of extreme sensitivity to daylight.

Clinically, the PDT treatment comprises giving a particular chosen photosensitizing drug that is usually injected into the patient. A given delay time period specific to the particular drug is allowed to elapse. The time delay period allows the drug to reach the tumor tissue for light activation. The selective retention of the drug in the tumor tissue, as compared to healthy surrounding tissue, allows the eradication of the tumor tissue with minimal damage to healthy tissue. However, the dose of the drug must be carefully monitored in order to prevent the normal cells from developing a concentration of the photosensitive drug that would photosensitize such normal cells to the light dose. Similarly, the light dose must be set high enough to cause the target abnormal tumor cells to be destroyed with minimal damage to normal cells.

Each patient has an individual metabolic rate, body mass, fluid content, and cellular dynamics such that the concentration of the photosensitizing drug in the patient cannot be accurately determined without actual measurement. The concentration of the photosensitizing drug in the whole blood is a reliable indicator of the amount of drug that the cells have taken up. The cells take up each particular drug up to a certain known threshold concentration for each particular drug. Above a certain known maximum concentration for each particular drug, the concentration of the drug is too high in the normal cells, thus causing unacceptable damage to normal cells. The whole blood level therefore is an accurate indicator of when the amount of photosensitizing drug is correct for PDT.

Accordingly, the total content of the photosensitizing drug in the patient's whole blood must be determined in order that the dose of light be calculated for each patient for a given particular drug. However, current wet chemical or chromatographic techniques for assaying the content of a drug in blood takes too long for effective PDT use. The concentration of drug can easily change considerably in the time it takes to assay by conventional techniques. Furthermore, the conventional assaying techniques are expensive, demanding extensive laboratory and technical personnel support.

OBJECTS AND SUMMARY OF THE INVENTION

It is an object of the present invention to provide a method to assess a patient's total content of a photosensitizing drug in his blood as rapidly as possible.

It is an object of the present invention to provide a method to assess a patient's total content of a photosensitizing drug so that a clinician delivering PDT can adjust the light dosage so as to provide a light drug dose that will provide total efficacy.

It is an object of the present invention to provide a method that monitors the fluorescence of a photosensitizing drug used in PhotoDynamic Therapy from a whole blood sample, at the treatment light wavelength associated with the photosensitizing drug's use in PhotoDynamic Therapy, when excited at a shorter light wavelength than the treatment light wavelength in order to assay the amount of the drug in the whole blood sample. The assay amount is directly correlated with the amount of photosensitizing drug in a patient from which the blood sample was taken.

Briefly stated, a method for determining a concentration of a photosensitizing drug in a patient, for PhotoDynamic Therapy treatment of the patient by a treatment light at a treatment light wavelength, comprises the steps of drawing a blood sample from the patient, spreading the blood sample between two optically transmissive plates to form a spread sample, irradiating the spread sample with an interrogation light at an interrogation wavelength range of an absorption band bluer than the treatment light wavelength, measuring a magnitude of an emission signal at the treatment light wavelength, the emission signal caused by the irradiation of the spread sample, and comparing the measured magnitude to a magnitude/concentration calibration curve to determine the concentration of the photosensitizing drug.

According to an embodiment of the present invention, there is provided a method for determining a concentration of the photosensitizing drug in the patient, for PhotoDynamic Therapy treatment of the patient by a treatment light at a treatment light wavelength, the method comprising the steps of drawing a blood sample from the patient, spreading the blood sample between two optically transmissive plates to form a spread sample, irradiating the spread sample with an interrogation light in an interrogation wavelength range of an absorption band, of the photosensitizing drug, bluer than the treatment light wavelength, and measuring a magnitude of an emission signal at the treatment light wavelength, the emission signal caused by the irradiation of the spread blood sample, comparing the measured magnitude to a magnitude/concentration calibration curve to determine the concentration of the photosensitizing drug.

According to another embodiment of the present invention, there is provided a method for determining a concentration of the photosensitizing drug in the patient, for PhotoDynamic Therapy treatment of the patient by a treatment light at a treatment light wavelength, the method comprising the steps of drawing a blood sample from the patient, spreading the blood sample between two optically transmissive plates to form a spread sample, drying the spread sample to form a dried spread sample, irradiating the dried spread sample with an interrogation light in an interrogation wavelength range of an absorption band, of the photosensitizing drug, bluer than said treatment light wavelength, and measuring a magnitude of the measurable emission signal at the treatment light wavelength, the measurable emission signal caused by the irradiation of the dried spread sample, comparing the measured magnitude to a magnitude/concentration calibration curve to determine the concentration of the photosensitizing drug.

According to an embodiment of the present invention, there is provided a method for determining a concentration of the photosensitizing drug in the patient, for PhotoDynamic Therapy treatment of the patient by a treatment light at a treatment light wavelength, the method comprising the steps of drawing a calibrated blood sample from the patient, spreading the calibrated blood sample between two optically transmissive plates to form a spread sample, irradiating the spread sample with an interrogation light in an interrogation wavelength range of an absorption band, of the photosensitizing drug, bluer than the treatment light wavelength, and measuring a magnitude of an emission signal at the treatment light wavelength, the emission signal caused by the irradiation of the spread blood sample, comparing the measured magnitude to a magnitude/concentration calibration curve to determine the concentration of the photosensitizing drug.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 1 is a diagram representing the method of the present invention.

DETAILED DESCRIPTION OF THE PREFERRED EMBODIMENT(S)

The method of the present invention utilizes a simple fluorescence apparatus which allows a near instant readout. The method incorporates a light source which is selectively tuned to a given wavelength range needed to excite the drug used for a particular PDT. This technique is effective for drugs under all conventional PDT methodologies or new methodologies because inherent in PDT methodologies is the requirement that the drugs used be sensitive to light. Further, the treatment light wavelength is typically at the red region of the visible spectrum because tissue transmission of visible light is best at the red region. The interrogation light is set by examination of the visible (ultraviolet to near infrared) absorption spectrum of the particular drug being used for PDT. The interrogation light is set to an absorption band, in the absorption spectrum, of higher energy (to the blue side) of the treatment wavelength. The interrogation light is preferably of the wavelength range that is full width half height of the absorption feature of the absorption curve of the PDT drug.

The interrogation light causes the sample to emit an emission signal light, for example by fluorescence, at a lower wavelength than the interrogation light. The emission signal light is collected and its intensity measured.

The emission signal light can be measured at different wavelengths that can be determined through examination of the spectral emission curves for each particular PDT drug in order to determine the effective emission signal wavelength. However, such preparation is not necessary because the method of the present invention uses the very same wavelength that will be used for the PhotoDynamic Therapy itself as the effective emission signal wavelength. Therefore, all drugs used in PDT are easily and effectively assayed by the method of the present invention.

Referring to FIG. 1, in the method of the present invention a small amount, for example 1 drop, of blood is drawn in step 1 from the patient. The blood sample is spread between two optically transmitting plates, such as two microscope slides for example, in step 5. An optional procedure of step 5 includes allowing the spread blood sample to dry in a step 2. The spread blood sample is ready for direct fluorimetry. It is preferable that a specific calibrated amount of blood such as 1 drop be used. Although the use of optically transmissive plates generally causes the blood sample to form a uniformly consistent thickness so that a calibrated amount is not critical because plates are generally substantially flat, results are optimized with repeatable conditions.

The spreading of the blood sample is effective to cause the spread sample to emit a measurable emission signal at the treatment light wavelength when irradiated by the interrogation wavelength range at an absorption band bluer than the treatment light wavelength.

In the method of the present invention, an interrogation light source tuned to the excitation wavelength range of an absorption feature of the PDT photosensitive drug, is directed in step 3 towards the optical plates containing the spread blood sample. The interrogation light source is directed by any convenient means such as, for example, by fiber optics, mirrors, light channel guides, or prisms, individually or in combination. As recited above, the optical plates can be, for example, a microscope slides. Also as recited above, the excitation wavelength is an absorption wavelength to the blue of the wavelength that is used for PhotoDynamic Therapy for the particular drug. Step 4 shows the placement of optical components to modify the light in order to present the proper light intensity and wavelength to the spread blood sample of step 5. Such optics include a bandpass filter or monochromator when the light source is broadband in order to allow through the proper interrogation light. Such bandpass filters should preferably pass through the full width half height of the absorption feature of the absorption curve of the PDT drug. The monochromator should be set to the peak of the absorption feature. Such optics can include lenses and prisms to spread and collimate the beam, particularly is the interrogation beam is a laser beam.

The emission signal is collected at an off-angle, such as 90 degrees, from the interrogation light path and modified by optical components in step 6 of the present invention. The collection can be by any convenient means such as, for example, by fiber optics, mirrors, light channel guides, or prisms, individually or in combination. The emission signal wavelength is the same wavelength as that used for the PhotoDynamic Therapy. The optics include a bandpass filter or a monochromator in order to pass through the wavelength of the PhotoDynamic Treatment light. The optics serve also to block the interrogation light. The bandpass filter is preferably a filter centered at the treatment wavelength that lets through light about 10 mm to either side of the treatment wavelength.

The emission signal light is detected in step 7 by a detection device situated at an off angle such as, for example, a right angle to the interrogation light source. The detection device collects the emission from the sample at the PhotoDynamic Therapy treatment wavelength.

In a preferred geometry, the two optical plates holding the spread blood sample is placed at a 45 degree tilt to the optical axis of the interrogating light. Thus the interrogating light is partially transmitted along the optical axis through the spread blood sample and partially reflected off in a direction at a transverse axis right angle to the optical axis. The reflected interrogation light is reflected from the front surfaces of the optical plates. Consequently, there is little interrogation light that is directed in the direction at a transverse axis away from the back of the optical plates—that is, in the opposite direction from the interrogation light reflected off the front surfaces. The detection device is placed at the transverse axis but at this opposite other direction from the front reflected interrogating light.

The apparatus is calibrated by preparing a calibration curve from standard whole blood spread samples prepared with the particular photosensitizing drug being used for PDT. The standard spread samples are samples, spread between optical plates, of whole blood with known concentrations of the particular photosensitizing drug. The emissions signal for each prepared spread sample is plotted against the known concentration of the drug in the prepared spread samples. The calibration curve is prepared in step 8 of FIG. 1.

In step 9, the signal intensity from step 7 is compared with the calibration curve of step 8. Such comparison can be any convenient means such as being made by eye or by computer program. The result is presented in step 10 by any convenient means such as being a point on the calibration curve wherein the value of the concentration is read out or as a number shown on a computer display.

The method of the present invention has been tested extensively, utilizing several configurations including a conventional fluorimeter (Shimadzu model RF-540) and a custom built fluorimeter that uses a filtered Zeiss illuminator (Schott glass filter), a detector comprising a photodiode which was also filtered (Schott glass filter), with a readout provided by a Digital Volt Meter (DVM). In all cases, the method of the present invention quickly and effectively determined the concentration of any PDT drug.

It can be seen that the method of the present invention relies on only one aspect for its efficiency, accuracy, and precision. That is that the apparatus must be calibrated, prior to clinical measurement, with known whole blood calibrated samples, spread between optical plates, of the same photosensitizing drug that is being used for the PDT treatment. As recited above, a calibration curve is prepared from the standard whole blood samples spread between optical plates and is used to read off the exact concentration of the patient's blood sample. A typical assay would take less than five minutes from the time of drawing of the blood sample to the reporting of the drug concentration.

There are a number of known ways to prepare a calibration curve with precision. For example, the emission strength/drug concentration points can be plotted on graph paper. Another example is to statistically set a calibration curve in the computer of the fluorimeter so that the calibration curve is directly accessed from the instrument's interface. Serial addition of photosensitizing drug to the blood sample increases precision.

The method of the present invention has been tested a number of times on both animal and human blood samples, utilizing a conventional spectrofluorimeter as well as a custom made solid state single frequency device and has been found to be reliable, repeatable, and accurate down to doses as low as picograms/milliliters. This sensitivity is thousands of times more than that necessary to assay human blood samples which, for the drugs presently available, normally range from hundreds of nanograms to micrograms per milliliter.

The spread sample can be allowed to dry without affecting the effectiveness of the method of the present method. It is preferred to assay directly on the undried spread blood sample because it saves the time of drying. However, several samples can be prepared for assaying before being presented to the interrogating light. In such cases, the samples can dry while waiting for time in the assaying fluorimetry apparatus. Therefore, the samples can be at various stages of drying without affecting the effectiveness of the present invention. The method of the present invention depends on the total number of drug molecules interrogated by the interrogating light. Hence, the drying of the blood sample between the two optical plates does not measurably affect the number of drug molecules interrogated. There is no migration of drug molecules from the spread sample because the drug molecules are of fairly high molecular weight relative to the water.

The method of the present invention will work even when the interrogation light is a light source such as a laser or monochrome light source that does not require optical treatment before being directed at the whole blood sample. The method of the present invention will work even when the interrogation light source inherently has a wavelength range that is narrower than the absorption feature of the interrogation. The method of the present invention will also work even when the detector inherently is unresponsive to wavelengths other than the signal emission wavelength.

Although the present method will give a fast and accurate assay, good clinical practice can require two or more determinations in order to have verification of the initial measured value.

Having described preferred embodiments of the invention with reference to the accompanying drawing, it is to be understood that the invention is not limited to those precise embodiments, and that various changes and modifications may be effected therein by one skilled in the art without departing from the scope or spirit of the invention as defined in the appended claims.

What is claimed is:

1. A method for determining a concentration of a photosensitizing drug in a patient, for PhotoDynamic Therapy treatment of said patient by a treatment light at a treatment light wavelength, said method comprising the steps of:

drawing a whole blood sample from said patient;

spreading said whole blood sample between two optically transmitting plates to form a spread sample containing some amount of a photosensitizing drug including none;

irradiating said spread sample with an interrogation light in an interrogation wavelength range of an absorption band, of said photosensitizing drug, bluer than said treatment light wavelength;

measuring a magnitude of an emission signal at said treatment light wavelength, said emission signal caused by said irradiation of said spread sample; and comparing said measured magnitude to a magnitude/concentration calibration curve to determine the concentration of said photosensitizing drug.

2. A method according to claim 1 for determining a concentration of a photosensitizing drug in a patient, wherein said interrogation light is a laser light, in said step of irradiating.

3. A method according to claim 1 for determining a concentration of a photosensitizing drug in a patient, wherein said interrogation light is a filtered light, in said step of irradiating.

4. A method according to claim 1 for determining a concentration of a photosensitizing drug in a patient, wherein said interrogation light is a light from a monochromator, in said step of irradiating.

5. A method according to claim 1 for determining a concentration of a photosensitizing drug in a patient, wherein said method further comprises a step of filtering an emission light from said irradiated spread sample followed by a step of converting said filtered emission light to a measurable emission signal; and said steps of filtering and converting being prior to said step of measuring.

6. A method according to claim 5 for determining a concentration of a photosensitizing drug in a patient, wherein said step of filtering is performed with a narrow bandpass filter centered at said treatment light wavelength and passing light about 10 nm to each side of said treatment light wavelength.

7. A method for determining a concentration of a photosensitizing drug in a patient, for PhotoDynamic Therapy treatment of said patient by a treatment light at a treatment light wavelength, said method comprising the steps of:

drawing a whole blood sample from said patient;

spreading said whole blood sample between two optically transmitting plates to produce a spread sample containing some amount of a photosensitizing drug including none;

drying said spread sample to produce a dried spread sample;

irradiating said dried spread sample with an interrogation light in an interrogation wavelength range of an absorption band, of the photosensitizing drug, bluer than said treatment light wavelength;

measuring a magnitude of a measurable emission signal at said treatment light wavelength, said measurable emission signal caused by said irradiation of said dried spread sample; and comparing said measured magnitude to a magnitude/concentration calibration curve to determine the concentration of said photosensitizing drug.

8. A method according to claim 7 for determining a concentration of a photosensitizing drug in a patient, wherein said interrogation light is a laser light, in said step of irradiating.

9. A method according to claim 7 for determining a concentration of a photosensitizing drug in a patient, wherein said interrogation light is a filtered light, in said step of irradiating.

10. A method according to claim 7 for determining a concentration of a photosensitizing drug in a patient, wherein said interrogation light is a light from a monochromator, in said step of irradiating.

11. A method according to claim 7 for determining a concentration of a photosensitizing drug in a patient, wherein said method further comprises a step of filtering an emission light from said irradiated dried spread sample followed by a step of converting said filtered emission light to said measurable emission signal; and said steps of filtering and converting being prior to said step of measuring.

12. A method according to claim 11 for determining a concentration of a photosensitizing drug in a patient, wherein said step of filtering is performed with a narrow bandpass filter centered at said treatment light wavelength and passing light about 10 nm to each side of said treatment light wavelength.

13. A method for determining a concentration of a photosensitizing drug in a patient, for PhotoDynamic Therapy treatment of said patient by a treatment light at a treatment light wavelength, said method comprising the steps of:

drawing a calibrated whole blood sample from said patient;

spreading said calibrated whole blood sample between two optically transmitting plates to form a spread sample containing some amount of a photosensitizing drug including none;

irradiating said spread sample with an interrogation light in an interrogation wavelength range of an absorption band, of said photosensitizing drug, bluer than said treatment light wavelength;

measuring a magnitude of an emission signal at said treatment light wavelength, said emission signal caused by said irradiation of said spread sample; and comparing said measured magnitude to a magnitude/concentration calibration curve to determine the concentration of said photosensitizing drug.

14. A method according to claim 13 for determining a concentration of a photosensitizing drug in a patient, wherein said interrogation light is a laser light, in said step of irradiating.

15. A method according to claim 13 for determining a concentration of a photosensitizing drug in a patient, wherein said interrogation light is a filtered light, in said step of irradiating.

16. A method according to claim 13 for determining a concentration of a photosensitizing drug in a patient, wherein said interrogation light is a light from a monochromator, in said step of irradiating.

17. A method according to claim 13 for determining a concentration of a photosensitizing drug in a patient, wherein said method further comprises a step of filtering an emission light from said irradiated spread sample followed by a step of converting said filtered emission light to said emission signal; and said steps of filtering and converting being prior to said step of measuring.

18. A method according to claim 17 for determining a concentration of a photosensitizing drug in a patient, wherein said step of filtering is performed with a narrow bandpass filter centered at said treatment light wavelength and passing light about 10 mm to each side of said treatment light wavelength.

* * * * *